July 21, 1959 H. M. TIRET Plant Pat. 1,855
FUCHSIA PLANT
Filed Nov. 28, 1958
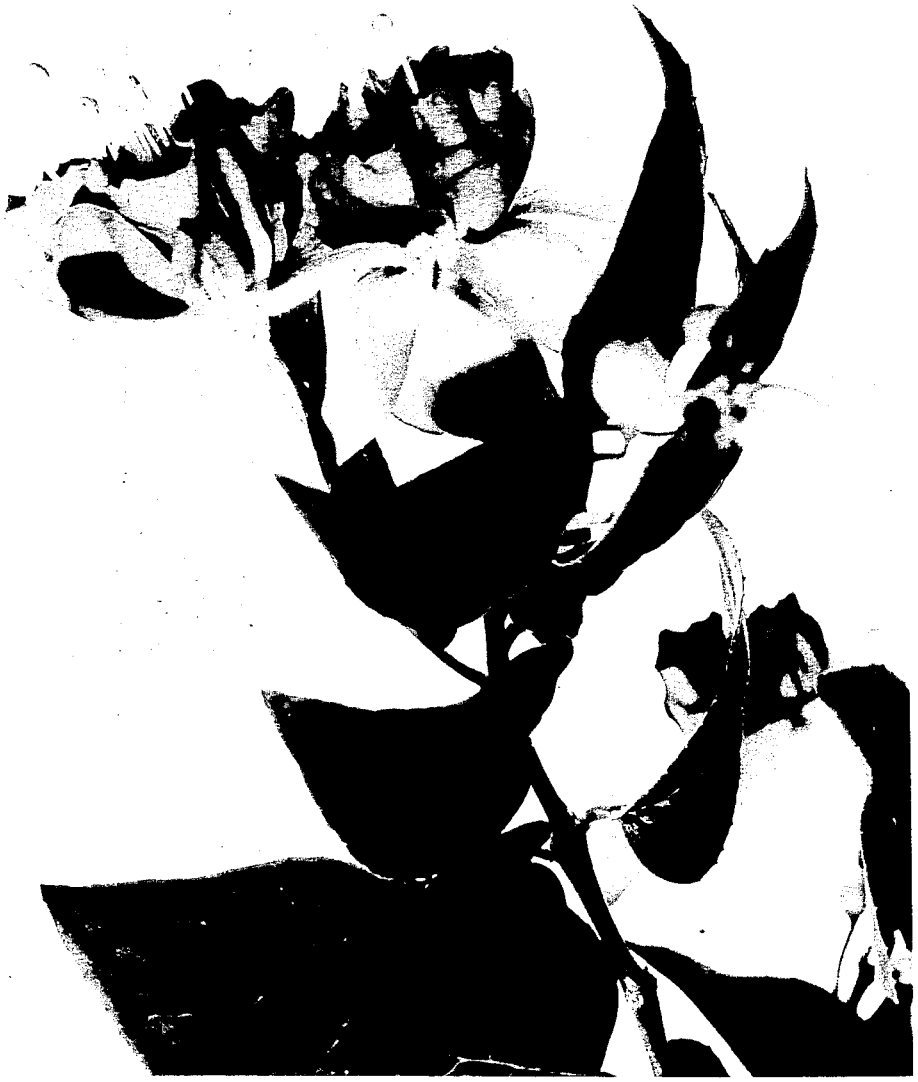

United States Patent Office

Plant Pat. 1,855
Patented July 21, 1959

1,855

FUCHSIA PLANT

Horace M. Tiret, San Francisco, Calif.

Application November 28, 1958, Serial No. 777,164

1 Claim. (Cl. 47—60)

This invention relates to a new and improved fuchsia plant, the principal new and different characteristic of which is the contrast of the white sepals and red double corolla in combination with an excellent trailing habit of growth.

The accompanying color photograph illustrates the plant in bloom and the aforementioned new and different characteristic.

The plant was derived as a hybrid from a seedling (unpatented, not introduced to the trade), namely, 7/23/5, the figures representing applicant's own breeding symbols, and Old Smoky (unpatented). The fuchsia plant is distinguished principally by the contrast of sepals and double corolla, as above described. When the flower first opens, the petals are Indian Lake (British Horticultural Color Chart #826–3), changing with maturity to Spiraes Red (British Horticultural Color Chart #025). The color is solid during all stages of growth and at maturity. The sepals are white, with pale green tips. The fully open flower displays the red double corolla distinctive to the plant. The resulting effect is one not previously existing in any other fuchsia plant. The plant has been asexually reproduced at Colma, California, by cuttings which retained the characteristics of the parent fuchsia plant.

The plant has an excellent trailing habit of growth, and grows vigorously.

In the accompanying drawing, the figure shows a typical branch tip, the drawing representing approximate actual size.

A detailed description of this new variety of fuchsia plant follows:

*Habit of growth.*—Strong trailing variety which blooms early and vigorously.

*Foliage.*—The foliage is medium in size and medium green in color. The branches are greenish-brown. The mature leaf is approximately 3″ in length and one and three-quarters inches in width at the widest point at maturity. The outer surface has a very crinkly texture.

*Flowers.*—The flower has three stages of development and is different in color at each of those stages. At the first stage, when the flower opens, it is very deep in color with light sepals. At the next stage, the sepals are white with the corolla fading into light color, showing slight marbling effect. When fully opened, the sepals become more pink and the petals spread out widely, affording a pronounced marbling effect. Fully opened, the flower is exceptionally large. At the fully opened stage, the main petals are colored Mallow Purple (British Horticultural Color Chart #630), the inner area toward the base is Mallow Purple (British Horticultural Chart 630–3). The outer petals surrounding the main petals are splotched with Persian Rose (British Horticultural Chart #628–3), otherwise the color of the petals is similar to that of the main petals.

*Petals.*—Approximately 27 petals occur to each flower. The corolla is double and flaring (slightly), with petals tightly layered in a vertical position. The diameter of the open, mature flower is approximately 2″ and each of the large petals is approximately 1¼″ in length by ⅞″ in width at the widest point. The color of the petals is solid, as described above.

*Ovary.*—Bright green in color, length approximately 10¾″, width at widest point approximately ⅞″, measured at maturity.

*Tube.*—White with greenish cast on the immature flower. The tube is medium long and narrow, being approximately ⅞″ in length, and ¼″ in width, at the widest point, measured at maturity.

*Sepals.*—The sepals are four in number, approximately 1¼″ in length and ⅞″ in width at the widest point, measured at maturity. In form the sepals are medium broad, being at a horizontal position when the flower is at maturity. The underside has slightly crepe-like texture, while the outer side is satiny in appearance with a smoother texture.

*Pistil.*—The style is approximately 2½″ in length, and 1/32″ in width, measured at maturity. The style is carmine in color, and the stigma is white.

*Stamens.*—The stamens are eight in number, flesh colored, as are the anthers. They are 1½″ in length, measured at maturity, and slender.

*Parentage.*—Applicant's own seedling (unpatented) not introduced to the trade, applicant's breeding symbols 7/23/5 and Old Smoky (unpatented).

It is noted that the foliage and flowers will vary somewhat with the seasons and growing conditions; however, the fuchsia plant is thoroughly differentiated from others by reason of the distinguishing characteristics herein described.

Having thus disclosed my discovery, I claim:

The new and distinct variety of fuchsia plant herein described and illustrated, characterized by the form and attractive color of the red double corolla, contrasting with the sepals, as combined in a plant having an excellent trailing habit of growth.

No references cited.